United States Patent
Lamey et al.

(10) Patent No.: US 7,396,649 B2
(45) Date of Patent: Jul. 8, 2008

(54) MIGRAINE AND VASODILATION TREATMENT

(75) Inventors: Philip-John Lamey, Hollywood (GB); Fionnuala Teresa Lundy, Belfast (GB); Christopher Shaw, Comber (GB)

(73) Assignee: Philip-John Lamey, Holywood (GB)

( * ) Notice: Subject to any disclaimer, the term of this patent is extended or adjusted under 35 U.S.C. 154(b) by 844 days.

(21) Appl. No.: 10/257,435

(22) PCT Filed: Apr. 17, 2001

(86) PCT No.: PCT/GB01/01683

§ 371 (c)(1),
(2), (4) Date: Feb. 26, 2003

(87) PCT Pub. No.: WO01/79270

PCT Pub. Date: Oct. 25, 2001

(65) Prior Publication Data

US 2004/0092439 A1 May 13, 2004

(51) Int. Cl.
*G01N 33/53* (2006.01)
(52) U.S. Cl. ............. 435/7.1; 530/387.9; 530/830; 435/23
(58) Field of Classification Search ........... 435/7.1; 530/387.9, 830
See application file for complete search history.

(56) References Cited

FOREIGN PATENT DOCUMENTS

| WO | 94/15578 | 7/1994 |
|----|----------|--------|
| WO | 00/08159 | 2/2000 |
| WO | WO 01/68851 | 9/2001 |

OTHER PUBLICATIONS

Bobek et al., Biochem. J. (1991). vol. 278. pp. 627-635.*
Palsdottir et al., The Lancet. Sep. 10, 1988. pp. 603-604.*
Baron et al., Oral Diseases. 1999. vol. 5. pp. 344-353.*
Blankenvoorde et al., Journal of Periondontal Research. 1997. vol. 32. pp. 583-588.*
Bobek, L.A., et al: "Cystatins—Inhibitors of Cysteiene Proteinases" *Critical Reviews in Oral Biology and Medicine*, CRC Press, Boca Raton, FL, US, vol. 3, No. 4, pp. 307-332 (1992).
Goadsby, "Neuroimaging in Headache" *Microscopy Research and Technique*, 53, 179-187 (2001).
Shi, et al., "Cystatin C deficiency in human atherosclerosis and aortic aneurysms" *J. Clin. Invest.* 104, 1191-97 (1999).
Williamson, et al. "The novel anti-migraine agent rizatriptan inhibits neurogenic dural vasodilation and extravasation" *Eur. J. Pharmacol.*, 328, 61-64 (1997).
Williamson, et al. "Role of opioid receptors in neurogenic dural vasodilation and sensitization of trigeminal neurons in anaesthetized rats" *Brit. J. Pharmacol*, 133, 807-14 (2001).
Goadsby, "Neuroimaging in Headache" *Microscopy Research and Technique*, 53, 179-187 (2001).
Shi, et al., "Cystatin C deficiency in human atherosclerosis and aortic aneurysms" *J. Clin. Invest.* 104, 1191-97 (1999).
Williamson, et al. "The novel anti-migraine agent rizatriptan inhibits neurogenic dural vasodilation and extravasation" *Eur. J. Pharmacol*, 328, 61-64 (1997).
Williamson, et al. "Role of opioid receptors in neurogenic dural vasodilation and sensitization of trigeminal neurons in anaesthetized rats" *Brit. J. Pharmacol*, 133, 807-14 (2001).

* cited by examiner

*Primary Examiner*—Bao-Thuy L. Nguyen
(74) *Attorney, Agent, or Firm*—Drinker, Biddle & Reath

(57) ABSTRACT

The present invention related to the use of Cystatin in predicting onset of migraines. The invention also relates to the use of Cystatin as a vasodilatory agent. The invention also relates to antagonists to Cystatin for use in treating and preventing and treating migraine attacks.

5 Claims, No Drawings

SEQUENCE LISTING

```
<160> NUMBER OF SEQ ID NOS: 2

<210> SEQ ID NO 1
<211> LENGTH: 141
<212> TYPE: PRT
<213> ORGANISM: Homo Sapiens

<400> SEQUENCE: 1

Met Ala Gln His Leu Ser Thr Leu Leu Leu Leu Ala Thr Leu Ala
1               5                   10                  15

Val Ala Leu Ala Trp Ser Pro Lys Glu Glu Asp Arg Ile Ile Pro Gly
            20                  25                  30

Gly Ile Tyr Asn Ala Asp Leu Asn Asp Glu Trp Val Gln Arg Ala Leu
        35                  40                  45
```

```
                                  -continued

His Phe Ala Ile Ser Glu Tyr Asn Lys Ala Thr Lys Asp Asp Tyr Tyr
    50                  55                  60

Arg Arg Pro Leu Arg Val Leu Arg Ala Arg Gln Gln Thr Val Gly Gly
65              70                  75                  80

Val Asn Tyr Phe Phe Asp Val Glu Val Gly Arg Thr Ile Cys Thr Lys
                85                  90                  95

Ser Gln Pro Asn Leu Asp Thr Cys Ala Phe His Glu Gln Pro Glu Leu
            100                 105                 110

Gln Lys Lys Gln Leu Cys Ser Phe Glu Ile Tyr Glu Val Pro Trp Glu
        115                 120                 125

Asn Arg Arg Ser Leu Val Lys Ser Arg Cys Gln Glu Ser
    130                 135                 140

<210> SEQ ID NO 2
<211> LENGTH: 28
<212> TYPE: PRT
<213> ORGANISM: Artificial Sequence
<220> FEATURE:
<223> OTHER INFORMATION: Fragment of Human Cystatin

<400> SEQUENCE: 2

Ile Ile Pro Gly Gly Ile Tyr Asn Ala Asp Leu Asn Asp Glu Trp Val
1               5                   10                  15

Gln Arg Ala Leu His Phe Ala Ile Ser Glu Tyr Asn
            20                  25
```

MIGRAINE AND VASODILATION TREATMENT

The present invention relates to a novel biochemical marker associated with migraine and a method of predicting forthcoming migraine attacks. The invention also relates to a novel vasodilatory agent and to the use of a peptide to develop an antimigraine therapy.

The molecular basis of migraine was previously unknown. Work in this area began with the clinical observation that most migraineurs woke with a migraine from sleep. This cast considerable doubt on the previously described relationship between migraine and so called trigger factors such as the ingestion of cheese, chocolate, citrus fruits and red wine for two reasons: firstly, the time scale was too long as patients normally sleep for 6-8 hours and yet a pharmacological effect of an ingredient of these substances should produce and effect within 1-2 hours and secondly, critical evaluation of the evidence for these factors actually triggering true migraine is weak.

In view of these observations, investigations were carried out regarding factors during sleep which could conceivably trigger attacks of migraine. The resulting research identified tooth clenching as the major problem and this led to an appliance being described which obviated tooth clenching during sleep and in turn prevented attacks of migraine. Indeed following one year of treatment with such a device, around 85% of migraineurs suffer no further attacks.

Whilst deciding how long a patient had to wear the appliance in order to permanently alleviate their migraine, it became clear that a three month period was too short. Indeed all patients who discontinued their attacks by that time will experience an attack of migraine within ten days of stopping appliance therapy. In essence the appliance could therefore be used as a mechanism to trigger migraine in those individuals.

In a first aspect the present invention aims to provide a product to predict the onset of migraine.

The invention provides a method of predicting the onset of migraine attack, through the detection of elevated levels of salivary peptide Cystatin SN.

Following the establishment of a patient's normal Cystatin levels, variations of this level can serve as an indication of an impending attack of migraine.

According to the present invention there is provided a method for predicting potential migraine attacks, the method comprising the steps of establishing a normal level of Cystatin SN for an individual and subsequently testing for variations thereof wherein elevated levels of Cystatin SN indicate the on set of a migraine attack.

Elevated levels of Cystatin SN will preferably be at least three time the normal levels.

Prediction of a migraine attack will enable an individual to commence treatment of the attack before onset therefore minimising any ill-effects or to plan ahead accordingly.

The method may extend to detecting levels of other members of the Cystatin family.

The detection method may look for the amino acid sequence which is known for Cystatin SN. The invention further provides a device for use in detecting elevated levels of Cystatin SN.

In one embodiment the device uses antibodies to Cystatin SN.

The device may be in the form of a dipstick.

The device may indicate changes of the level of Cystatin SN by colour change.

The invention may comprise use of an anti-sense RNA to the mRNA for Cystatin SN.

The invention comprises the use of the amino acid sequence of Cystatin SN in the elucidation of the or a nucleic acid sequence in the development of a test for elevated expression of Cystatin SN.

The invention provides such a test for detection of levels of expression of the Cystatin SN gene.

Data undertaken blindly on saliva samples from migraineurs and non-migraineurs has for the first time identified a reliable biochemical marker for migraine. To date no other substance has been so strongly linked to the disease process.

Presently there are no reliable markers for migraineurs nor biochemical predictive markers of attacks for an impending attack of migraine.

By having a model to trigger migraine attacks, the present inventors were able to identify a peptide in saliva which appears to be associated with migraines. The identified peptide was partially sequenced and the sequence was shown to be homologous with the known sequence of salivary peptide Cystatin SN.

The present inventors have found that levels of Cystatin SN are about ten times higher in migraineurs than non-migraineurs and levels rose markedly in the 24 hours before a migraine attack.

As this molecule is intimately linked with migraine attack, it can be concluded that its release as a result of tooth clenching may be the main factor responsible for attacks of migraine.

The amino-acid sequence of the identified peptide accords with that of the full sequence of Cystatin SN. This molecule offers for the first time the opportunity to reliably predict the onset of migraine attacks within a 24 hour period and as such has important implications for the management of migraineurs. FIG. 1 (SEQ ID NO.: 1) show the full amino-acid sequence of the Cystatin molecule.

As the full structure of Cystatins are known and the levels which are normally present in migraineurs are known as opposed to non-migraineurs, then a saliva based recording technique can be developed which quantifies the amount of Cystatin present in saliva. Such a technique would give the advantage that an individuals "baseline" Cystatin level could be established, and from this level changes associated with the subsequent development of an attack could be monitored, thus allowing forthcoming migraines to be predicted.

It is a further object of the present invention to provide a new vasodilatory molecule.

According to another aspect of the present invention there is provided a novel vasodilatory agent, wherein said novel, vasodilatory agent is or is based on the peptide Cystatin.

Studies linking the release of Cystatin SN with the onset of a migraine attack have shown that migraine attacks are related to profound vasodilation. The effectiveness of Cystatin SN as a vasodilator has been tested in vitro in an animal model system. This has shown that even crude extracts of saliva from migraineurs are vasodilatory and therefore it would be anticipated that refined preparations would show an even greater vasodilatory effect.

The invention further provides a method of controlling the degree of vascular tone by means of supplementing rational levels of Cystatin in the systemic circulation.

Preferably said vasodilatory agent may be administered as a potential application to a number of vasodilatory cardiovascular problems.

Preferably the invention will not be limited solely to Cystatin SN with any suitable peptide of the Cystatin group of peptides or synthetic versions or derivatives thereof being suitable for use.

The invention further provides use of Cystatin or a similar peptide in the preparation of a medicament for the treatment of vasodilatory problems.

By similar peptide is meant a peptide having a similar sequence which is prepared from nature or made synthetically or an active fragment thereof. An active fragment will have vasodilatory activity.

Preferably, said Cystatin would include the amino-acid sequence: I I P G G I Y N A D L N D E W V Q R A L H F A I S E Y N [SEQ ID NO.:2]

The amino-acid sequence of Cystatin is shown in FIG. 1 (SEQ ID NO.: 1).

Peptides being at least 60% homologous across the sequence should also be effective vasodilators.

The invention also provides a cDNA sequence which can be expressed to produce Cystatin or a similar peptide for use as a vasodilator.

The cDNA sequence may be used in the preparation of a medicament for the treatment of vasodilatory problems.

There are a number of conditions in which vasoconstriction produces a disease process such as ischaemic heart disease and peripheral vascular disease. The initial administration of Cystatin SN to in vivo and in vitro animal systems would allow careful evaluation of the degree of vasodilation caused by Cystatin SN and therefore its potential pharmacological effects.

Cystatin SN occurs naturally in low amounts in non-migraineurs. The levels of systemic circulation are likely to control the degree of vascular tone in vasodilation and therefore this could be supplemented by exogenous emission of Cystatin SN.

The present invention characterises the relationship between Cystatin SN as a vasodilatory neuro-peptide and its potential application to a number of vasodilatory cardiovascular related problems.

As Cystatin SN is a naturally occurring substance, the clinical response should be beneficial, but requires evaluation in a model system, particularly model systems which look at intra-cranial vasodilation.

Although the inventors do not wish to be bound by any particular theorem, the invention would be put into practice by using molecular techniques which involve cloning the substance and producing large volumes of it. Following this, the relative vasodilatory effect of the peptide versus other similar peptides would be tested in in vitro animal model systems. At the same time baseline levels of Cystatin SN both in saliva and in serum would be evaluated in migraineurs and non-migraineurs with this, followed by the administration of Cystatin SN perhaps initially by means of topical application to assess its vasodilatory effect. These effects would be further analysed both from a laser doppler point of view and also using the technique of thermographic imaging which allows non-invasive assessment of the degree of local vasodilation produced by the substance.

It is a further object of the present invention to provide a novel therapy for use in migraine management or prevention.

Migraine is currently managed in a number of ways. Although patients are often advised to avoid the so called trigger factors as detailed above, it is the inventor's opinion that this rarely solves the problem. Drug therapy is a standard way of managing migraine attacks and by and large there are two main drug therapies employed. One type of treatment comprises the administration of prophylactic drugs which can involve drugs such as beta-blockers which are given on an everyday basis, but the rationale and evidence that these are effective is not strong. The other way in which drugs can be used to treat an attack is through treating the attack at the acute stage. The problem with treatment at this stage, is that by definition the patient has to suffer an attack before acute drug therapy can be introduced. Therefore although acute drug therapy has some merit in reducing the severity of attacks, it is unable to prevent the frequency of attacks by its very nature of administration.

There are several disadvantages to current drug therapies. Firstly, the evidence for prophylactic anti-migraine drug therapy being effective is not strong and secondly the role of acute drug treatment suffers from the limitation that the patient has to actually suffer an attack before by definition they can be treated. An additional disadvantage is that in approximately 50% of such cases, treatment with the so called triptan drugs, patients suffer a rebound headache within 24 hours.

The present inventors have shown that the substance Cystatin SN is intimately linked to attacks of migraine. This offers the opportunity to investigate the mechanism by which Cystatin SN causes attacks of migraine and therefor offers new drug possibilities as an agent for developing a drug against Cystatin SN or its receptor or increasing drug metabolism or excretion or allowing current drug therapies, some of which are not presently indicated for use in the treatment of migraine, to be given at an earlier stage when they perhaps would be effective.

As there are no current reliable biochemical markers for migraine and there is some doubt as to the mechanism by which even acute migraine drug therapy is effective and as such the present invention in conjunction with the identification of the Cystatin SN molecule offers a different mechanism to prevent migraine attack.

The present invention thus provides the use of a Cystatin molecule in developing a treatment for migraine wherein the treatment is based on an antagonist of cystatin.

According to the present invention there is provided a method of treating or preventing onset of migraine attack, the method comprising the step of administering an antagonist to the molecule Cystatin.

Further, said method may extend to preventing migraine attack through the administration of an antagonist against any member of the family comprising Cystatin molecules.

Preferably the antagonist will be directed against the known amino acid sequence of Cystatin SN.

The invention also provides the use of Cystatin in the preparation of an antagonist thereto for the preparation of a treatment for migraine attacks.

The invention thus provides an antagonist to Cystatin.

The invention further provides the use of an antagonist to Cystatin in the preparation of a medicament for the treatment of migraine.

The invention also provides a cDNA clone for expression and production of Cystatin for use in the preparation of an antagonist thereto.

The amino-acid sequence of Cystatin is shown in FIG. 1 (SEQ ID NO.: 1).

Although the inventors do not wish to be bound by any particular theorm, the present invention may have the use and advantages as described below.

Prophylactic drug therapy is not effective and as such was not considered to be a fruitful avenue to pursue in terms of the mechanism of the drugs currently against Cystatin SN. However, detailed studies by the inventors on the effects of Cystatin SN on blood vessels have shown a relationship to angiotensin converting inhibitors. Interestingly, we note from our literature searches that these drugs are frequently associated with attacks of migraine. It is therefore proposed to either administer current acute phase therapies in a different way following a known prediction of an attack, or alternatively to look at other drugs which are effective against antiogtensin converting enzymes and then therefore Cystatin SN.

Clinical trials would be required to test the efficacy of current triptan drug therapies against levels of Cystatin SN to show whether there was any specific mode of action directed against Cystatin SN levels or alternatively whether there is any indirect action. This work would establish whether the effect of these drugs is truly via an effect on antagonism to Cystatin SN. The apparently very long half-life of Cystatin SN may also partly explain why in approximately 50% of the patients who treat their migraine during the acute phase with triptan suffer a rebound headache.

Although the particular description above and associated experimental work relates to Cystatin, potentially any member of the Cystatin family may show linked effects to the onset of migraine and as such an antagonist against these would also be appropriate.

The basis for the invention is described with reference to the following experiments.

EXPERIMENT 1

Relationship between saliva from migraine sufferers and lack of periodontal disease.

Antibacterial activity of saliva from migraine sufferers.

TABLE 1

| Saliva dilution in water | Source - non-migraine sufferer | | | Migraine Sufferer | | |
|---|---|---|---|---|---|---|
| | B. frag | P. Ging | P. Int | B. frag | P. Ging | P. Int |
| 1 | H | N | N | H | N | N |
| 0.5 | H | N | S | H | N | S |
| 0.25 | H | N | M | H | N | M |
| 0.125 | H | H | H | H | N | M |
| 0.0625 | H | H | H | H | M | M |
| 0.03125 | H | H | H | H | M | M |
| 0 Control | H | H | H | H | H | H |
| No bacteria Control | N | N | N | N | N | N |

H = high levels of bacteria
M = medium levels
S = small level
N = no bacteria
B. Frag = Bacteriodes fragilis
P. Ging = Porphyromonas gingivalis
P. Int = Porphyromonas intermedius Microtitre wells were inoculated with $5 \times 10^4$ bacteria per well in 1 ml of media. 100 μl of nondiluted/diluted saliva was added as set out in the table. Wells were monitored after 48 hours for presence of bacterial growth.

Saliva from migraine sufferers did not appear to have an inhibitory effect on Bacteriodes fragilis but had a significant inhibitory effect on Porphyromonas gingivalis and Porphyromonas intermedius.

EXPERIMENT 2

The relationship between periodontal disease and migraine.

Prior to this study little was known about the relationship between periodontal disease and migraine. The clinical impression observed by the present inventors was that significant periodontal disease was an uncommon finding in patients referred for management of migraine.

Materials and Methods

Subjects who had been diagnosed as having migraine were identified from the computerised diagnostic database of patients referred to the Oral Medicine Clinic, School of Dentistry, Queen's University, Belfast. All subjects were free of medical conditions or drug therapies known to have an effect on the periodontium. In this study available radiographs were used and measurements of bone loss were made only on sites displaying clear and complete images of the teeth. Orthopantomographs were taken with Dupont Ultrafilm using one of three units OPG5 (Siemens, Bensheim, Germany), by one of two senior radiographers both of who had been trained at the School of Dentistry, Belfast. These radiographs were processed in a standard manner using a Durr-Dental AC245L processor (Siemens, Bensheim, Germany), Orthoceph (Planmeca, Finland) or Siemens Orthophos plus (Siemens, Bensheim Germany). Films were developed with a Agfa-Gevaert Curix 242S (Agfa, Leverkusen, Germany) processor.

Assessment of Radiographs

One investigator examined all the films blinded to the clinical details of the subjects. Radiographs were examined under standard conditions of lighting, using an illuminated light box and ×5 magnification. Alveolar bone levels on the mesial and distal aspects of each tooth, excluding third molars, were evaluated from the available radiographs and the percentage alveolar bone loss was recorded. The methodology has been previously described by (Mullally & Linden 1996). Bone loss was assessed as a percentage of the expected bone height, calculated to the nearest 10%, using a modification of the 5 point Schei ruler. Where there was any doubt a surface was assigned the lower value for bone loss. Each tooth was represented by the score for the worst affected surface. Third molars were excluded from the analysis.

Calibration and Reproducibility

There was a period of training during which guidelines were developed and as part of the definitive study measurement reproducibility was assessed. To ensure that bone loss was consistently measured 9 randomly selected radiographs were re-measured. There was exact correspondence of the original and repeated measurement for 81% of teeth examined A further 17% of scores were within 10% and the remaining 2% of scores within 20% of the original bone loss measurement. This indicated that the reproducibility of this method of assessing proximal alveolar bone loss was within acceptable limits.

Results

The study group (n=60) consisted of three groups of subjects, twenty with a diagnosis of migraine, twenty with a diagnosis of toothwear and twenty controls with neither migraine nor toothwear. All subjects were non-smokers free from medical conditions or drug therapy known to have an effect on the periodontium and the three groups were well matched for age and gender. The details of the three groups are described in Table 2. The distribution of males to females in the tooth wear group was 3:1. This was different to the migraine or control group in which females were predominant.

The mean score for bone loss for the migraine group was 9.6 (S.D. 6.4) which was statistically significantly lower than that for either the toothwear 14.4 (S.D. 6.1; p=0.037) or the control group 13.8 (S.D. 5.9; p=0.022).

Discussion

Based upon a radiographic analysis of proximal alveolar bone height in sixty subjects recruited from hospital clinics our results suggest that the severity of periodontitis is significantly less in migraineurs than in either age and gender matched healthy controls or individuals with toothwear.

The limitations of this study include the fact that the clinical diagnosis of migraine or toothwear was made by a number of clinicians who were not directly involved in the study and the specific criteria for each diagnosis may exhibit some inter-examiner variation. Controls were recruited from the Admissions Clinic in the School of Dentistry on the basis that they did not give a history of migraine at that time. The distribution of males to females was different in the toothwear group compared with the migraineurs and controls, however this reflects the prevalence of toothwear in these clinics.

Overall the bone loss experienced by all three groups were relatively low for their age however the significantly lower values in the migraine group compared with controls would merit further investigation to investigate the relationship between migraine and periodontal disease. The fact that a significant difference was evident in such small groups may be indicative of a relationship between migraine and periodontal disease. These data support the suggestion that migraine has a putative protective effect on the periodontium. One possibility was that neuropeptides which mediate changes found in migraine may spill over into the mouth. It was speculated that Substance P and Neurokinin, A which are released during a migraine attach had a role in protecting against alveolar bone loss.

It is concluded from this radiographic study that migraineurs have less alveolar bone than subjects with toothwear or healthy controls.

TABLE 2

Age and gender distribution of study population

| Status | Number | Mean Age | Males | Females |
|---|---|---|---|---|
| Controls | 20 | 51.7 (8.5) | 8 | 12 |
| Migraine | 20 | 47.6 (10.8) | 7 | 13 |
| Toothwear | 20 | 50.2 (9.3) | 15 | 5 |

EXPERIMENT 3

The present inventors used Substance P antisera initially to determine the levels of Substance P in saliva from migraineurs. Remarkably high levels were observed and suggested that the antibody was cross-reacting with another/other peptide(s). HPLC separation was carried out and fractions were dot blotted and reacted with Substance P antisera. Reacting fractions were further purified and sequenced. The sequence of the significantly reacting peptide was found to correspond to the peptide sequence of Cystatin SN. Further analysis indicated that the levels of Cystatin SN are about ten times higher in migraineurs than non-migraineurs.

EXPERIMENT 4

Triggering Migraine Attacks

The molecular basis of migraine was previously unknown. Work by the inventors in this area began with the clinical observation that most migraineurs woke with a migraine from sleep. This case considerable doubt on the previously described relationship between migraine and so called trigger factors such as the ingestion of cheese, chocolate, citrus fruits and red wine for two reasons: firstly, the time scale was too long as patients normally sleep for 6-8 hours and yet the pharmacological effects of an ingredient of these substances should produce an effect within 1-2 hours and secondly, critical evaluation of the evidence for these factors actually triggering true migraine is weak.

In view of these observations, investigations were carried out regarding factors during sleep which could conceivably trigger attacks of migraine. The resulting research identified tooth clenching as the major problem and this led to an appliance being devised which obviated tooth clenching during sleep and in turn prevented attacks of migraine. Indeed following one year of treatment with such a device, around 85% of migraineurs suffered no further attacks.

Whilst deciding on how long a patient had to wear the appliance in order to permanently alleviate their migraine, it became clear that a three month period was too short. Indeed all patients who discontinued their attacks in that time will experience an attack of migraine within ten days of stopping appliance therapy. In essence the appliance could therefore be used as a mechanism to trigger migraine in those individuals.

By having a model to trigger migraine attacks, the constituents of saliva were analysed and this led to the identification of a peptide which shows two main features. Firstly the level of this peptide is about ten times higher in migraineurs than non-migraineurs and secondly levels rose markedly in the 24 hours before a migraine attack. This peptide was isolated and sequenced and the sequence was shown to correspond with the known sequence of Cystatin SN.

---

The invention claimed is:

1. A method of monitoring an individual to predict potential migraine attacks, the method comprising the steps of:
   establishing a level of Cystatin SN for an individual at a first time point, and then
   testing for variations of the level of Cystatin SN at a later time point,
   wherein an elevated level of Cystatin SN at the later time point relative to the level of Cystatin SN at the first time point is predictive of the onset of a migraine attack.

2. The method as claimed in claim 1, wherein the levels of Cystatin SN are measured using antibodies to Cystatin SN.

3. The method as claimed in claim 1 wherein the levels of Cystatin SN are determined by detecting levels of expression of the Cystatin SN gene.

4. The method as claimed in claim 1 wherein an elevated level of Cystatin SN is at least three times a normal level.

5. The method as claimed in claim 1, wherein the levels of Cystatin SN measured are the levels in the saliva of the individual.

* * * * *